United States Patent
Falkenstein

(10) Patent No.: US 6,633,109 B2
(45) Date of Patent: Oct. 14, 2003

(54) DIELECTRIC BARRIER DISCHARGE-DRIVEN (V)UV LIGHT SOURCE FOR FLUID TREATMENT

(75) Inventor: Zoran Falkenstein, Foothill Ranch, CA (US)

(73) Assignee: Ushio America, Inc., Cypress, CA (US)

( * ) Notice: Subject to any disclaimer, the term of this patent is extended or adjusted under 35 U.S.C. 154(b) by 360 days.

(21) Appl. No.: 09/757,352

(22) Filed: Jan. 8, 2001

(65) Prior Publication Data

US 2002/0089275 A1 Jul. 11, 2002

(51) Int. Cl.⁷ .................................................. H01J 1/02
(52) U.S. Cl. ........................ 313/29; 313/163; 313/328
(58) Field of Search .............................. 313/16, 29, 33, 313/150, 163, 165, 166, 167, 171, 328

(56) References Cited

U.S. PATENT DOCUMENTS

| | | |
|---|---|---|
| 5,194,740 A | 3/1993 | Kogelschatz |
| 5,834,784 A | 11/1998 | Morgan |
| 6,087,774 A * | 7/2000 | Nakayama et al. ......... 313/607 |
| 6,150,755 A * | 11/2000 | Druz et al. .............. 313/359.1 |
| 6,201,355 B1 | 3/2001 | Morgan |
| 6,398,970 B1 * | 6/2002 | Justel et al. ................. 210/748 |
| 6,525,451 B1 * | 2/2003 | Hishinuma et al. .......... 313/234 |

FOREIGN PATENT DOCUMENTS

WO    WO 99/62104    12/1999

* cited by examiner

Primary Examiner—Eric C. McCall
(74) Attorney, Agent, or Firm—J. D. Harriman, II; Coudert Brothers LLP

(57) ABSTRACT

The present invention provides a DBD lamp used in fluid treatment systems, where the irradiated fluid is used as a low voltage outer electrode instead of a metallic wire mesh. This fluid is in direct contact with the lamp envelope which acts as a two-fold advantage. First, the fluid acts as a strong built-in cooling source. This allows the lamp to be driven at high voltage without forced cooling. Second, the replacement of the wire mesh as the outer electrode by fluid as well as the sleeve eliminates the absorption of radiation from the outer surface of the DBD-driven light source which more than doubles the efficiency of the DBD-driven light source. The inner high voltage electrode remains in the center of the coaxial tube assembly and provides high voltage across the gas to generate excimer formation.

12 Claims, 3 Drawing Sheets

DBD UV lamp / reactor system for water treatment typical photochemical reactor for UV irradiation of water side-on view of typical co-axial DBD lamp end-on view of typical co-axial DBD lamp

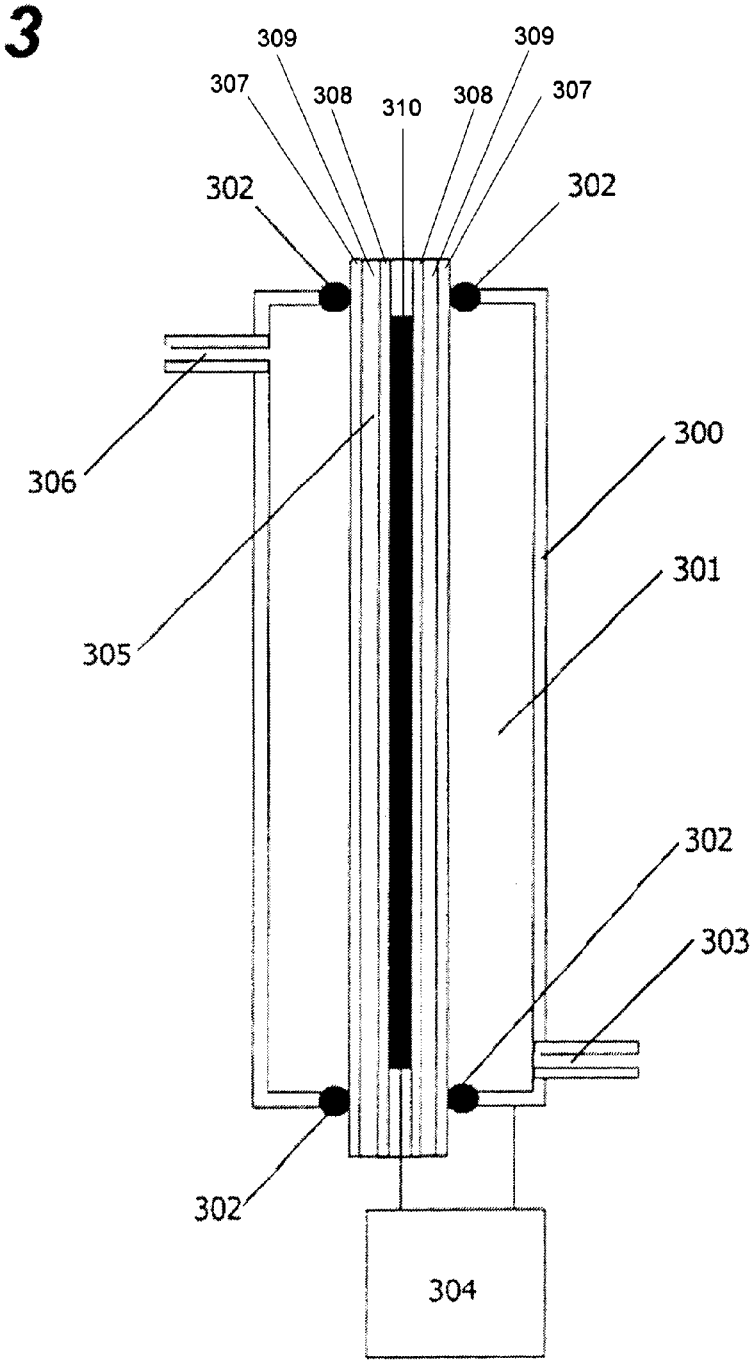
DBD UV lamp / reactor system for water treatment

DIELECTRIC BARRIER DISCHARGE-DRIVEN (V)UV LIGHT SOURCE FOR FLUID TREATMENT

BACKGROUND OF THE INVENTION

1. Field of the Invention

The present invention relates primarily to the field of water treatment UV systems, and in particular to a dielectric barrier discharge lamp used in fluid treatment UV systems, where the irradiated fluid is used as a low voltage outer electrode.

Portions of the disclosure of this patent document contains material that is subject to copyright protection. The copyright owner has no objection to the facsimile reproduction by anyone of the patent document or the patent disclosure as it appears in the Patent and Trademark Office file or records, but otherwise reserves all rights whatsoever.

2. Background Art

UV irradiating of water is a viable alternative to not only chlorinating water (especially drinking water) to disinfect it of harmful bacteria, but also for the degradation of organic compounds in fluids by advanced oxidation processes. UV irradiation is a mature alternative to chlorinating water because it eliminates the use of chemicals that may be allergic or harmful to the user. While disinfection of water can be primarily achieved by stand alone UV irradiation using UV light, advanced oxidation systems typically need a combination of UV light and oxidizing agents (ozone and/or hydrogen-peroxide) to reduce organic compounds found in certain fluids. Some advanced oxidation systems also include dispersed photo-catalysts, such as Iron (Fe) or Titanium (Ti) in addition to oxidation agents and UV light.

Using any of the above mentioned processes, the UV-treatment system must be able to effectively irradiate the fluid with (V)UV radiation since the (V)UV photons start the desired photo-physical or photo-chemical reaction.

Reactor Vessel

A cross-section of a typical reactor vessel with an imparted UV source used in the disinfection of water is shown in FIG. 1. Reactor vessel 101 is made out of metal, quartz, or glass, and forms the outer capsule. Infected water 102 enters the vessel via water inlet 103, and the disinfected water leaves the vessel via water outlet 107. The reactor vessel houses the UV source 106 which is encapsulated inside an inner sleeve 100 made out of quartz, or fused silica. The reactor vessel and sleeve are joined together at appropriate places using O-ring seals 105. The UV source is powered using power supply 104.

Currently such a system is widely used, for example, in the inhibition of the reproduction of bacteria in a germicidal system, for the radical formation through synthesis of organic compounds like ozone and/or hydrogen-peroxide, or the activation of a catalyst in a UV/oxidation system. Since the quantum efficiency of the processes mentioned above is maximized if the emitted radiation matches the light-induced process, intense and a spectrally selective radiation in a narrow wavelength range is desired. A dielectric barrier discharge (DBD) lamp is able to emit a spectrally selective radiation in a narrow wavelength range, and may be used as a UV source in a reactor vessel. A DBD lamp can be realized when applying a high voltage across a gas gap, which is separated from metallic electrodes by at least one dielectric barrier. Dielectric barriers include, for instance, glass or quartz. Due to the nature of the DBD lamp to generate non-thermal plasmas at atmospheric gas pressure, this kind of lamp is effectively used to produce excited diatomic molecules (excimers) when using rare gases, or mixtures of rare gases and halogens as the discharge gas. The excimer emits radiation in the ultraviolet spectral range when it decays (in vacuum), which is used for various photo-initiated or photo-sensitized applications for water treatment. FIGS. 2A and 2B provide an example of a typical DBD lamp.

DBD

FIG. 2A is a side view of a coaxial DBD lamp. The lamp envelope 200 is a transparent vessel that is typically made of glass or quartz. In common arrangements, an inner electrode 210, which is connected to a high voltage source, is separated from an outer mesh electrode 240, which is grounded. A loop of the dielectric barrier 220 touches both the inner and outer electrodes and space 230 created by the loop is filled with the plasma gases.

FIG. 2B provides an end-on view of the same coaxial DBD lamp shown in FIG. 1A. In FIG. 2B, it can be seen more clearly that the inner electrode 210 and the outer electrode 240 are circular in shape, and that the plasma gases 230 are sealed between the two electrodes.

In current systems, the use of a mesh electrode is essential for the outer electrode since the openings in the mesh allow the generated UV radiation to exit the UV source. Using a standard mesh wire electrode, the mesh typically covers 50% of the lamp, which results in a reduction in efficiency of 50%, since 50% of the excimers that are emitted from the DBD lamp will strike the mesh, and hence, will not be emitted into the fluid.

Radiant Efficiencies

The UV radiant efficiencies of a DBD driven excimer (V)UV light source depend on the electron densities and the electron distribution function, and can be "controlled" mainly by the applied voltage frequency and shape, gas pressure, gas composition, and gas gap distance. For the most efficient excimers $Xe_2$, XeCl, XeBr and KrCl, which emit narrow-banded or quasi-monochromatic UV light at 172 nm, 308 nm, 282 nm, and 222 nm, respectively, typical efficiencies are in the 8–15% range for sinusoidal high voltage and lamp arrangement (the efficiencies take into account the absorption of UV light by the metallic mesh electrode).

These efficiencies can double if steep-rising high voltage pulses can be generated, but a source that generates these steep-rising high voltage pulses is not readily available. Still, what makes this light source unique is that almost all of the radiation is emitted selectively. For photo-initiated or photo-sensitized processes, the emission can be considered quasi-monochromatic.

Many photo-physical and photo-chemical processes (e.g., UV curing and bonding, lacquer hardening, polymerization, material deposition, and UV oxidation) are initiated by a specific wavelength (ideally the excimer light source will emit close to those wavelengths). This light source can be far more effective than a high-powered light source when the emission suits the required wavelengths for a particular photo-physical or photo-chemical process, and this is desirable for certain applications like UV irradiation of water where specific wavelengths of light are needed.

Handicaps of Prior Art Systems

While the germicidal effect of UV radiation is very strong at 254 nm (which is the reason why UV disinfection systems for drinking water typically utilize the resonance radiation from low pressure mercury lamps at 254 nm), some UV disinfection and UV oxidation systems use intense, spectrally selective radiation at wavelengths other than 254 nm, which does not help in the disinfection of water. Unfortunately, with the exception of low-pressure mercury lamps, UV lasers, and dielectric barrier discharge (V)UV sources, no other intense, spectrally selective UV radiation sources are commercially available.

Commercially available intense UV sources are mainly medium and high pressure mercury lamps, Xe-arc, and flash lamps. All of these sources emit light in a broad spectral range. Therefore, if intense UV light other than the resonance radiation of mercury is desired in UV disinfection and UV oxidation systems, the only solution is to use a broadband or continuous UV source with the knowledge that only some of the emission will fall in the required critical wavelength range. Since most of the light is not needed, there is a lot of wastage.

Industrial Applicability

Various high-powered (V)UV light sources are presently being applied for different fluid treatment processes (such as disinfection and UV oxidation) in large scales. All of the applied (V)UV light sources—with the exception of low-pressure mercury lamps—emit radiation into a broad spectral range, although it has proven that only certain wavelengths are responsible for the photochemical process. Most of the emitted radiation is therefore lost.

As a result, there is a demand for high-powered (V)UV light sources that can emit selective wavelengths responsible for the desired photochemical processes. DBD lamps have emerged as such a (V)UV light source. Conventional DBD lamps, however, suffer the disadvantage that the outer mesh electrode severely inhibits the amount of light emitted from the DBD lamps. In addition, current high powered DBD lamps must undergo forced cooling which further complicates their usage in conventional UV treatment systems as depicted in FIG. 1.

SUMMARY OF THE INVENTION

The present invention relates to a DBD lamp used in fluid treatment systems, where the irradiated fluid is used as a low voltage outer electrode instead of a metallic wire mesh. One or more embodiments of the present invention uses an electrically conductive fluid, for example water that is not de-ionized, as a source of the grounded electrode for the DBD lamp. In one embodiment, the fluid is in immediate contact with the outer surface of the DBD lamp. In another embodiment, the inner high voltage electrode remains in the center of the coaxial tube assembly and provides high voltage across the gas to generate excimer formation. In yet another embodiment, the fluid, which is sealed against the lamp envelope by two O-ring seals, is flown through the discharge reactor for UV processing.

The direct contact of the fluid with the DBD light source provides a strong cooling for the high voltage lamp. Additionally, since the fluid is used as the outer electrode instead of the prior art wire mesh electrode, the amount of radiation emitted increases as there is no absorption by the metallic mesh or the quartz sleeve.

BRIEF DESCRIPTION OF THE DRAWINGS

These and other features, aspects and advantages of the present invention will become better understood with regard to the following description, appended claims and accompanying drawings where:

FIG. 3 is a cross-section of a DBD UV lamp/reactor system for fluid treatment according to the present invention.

DETAILED DESCRIPTION OF THE INVENTION

Figure 1:
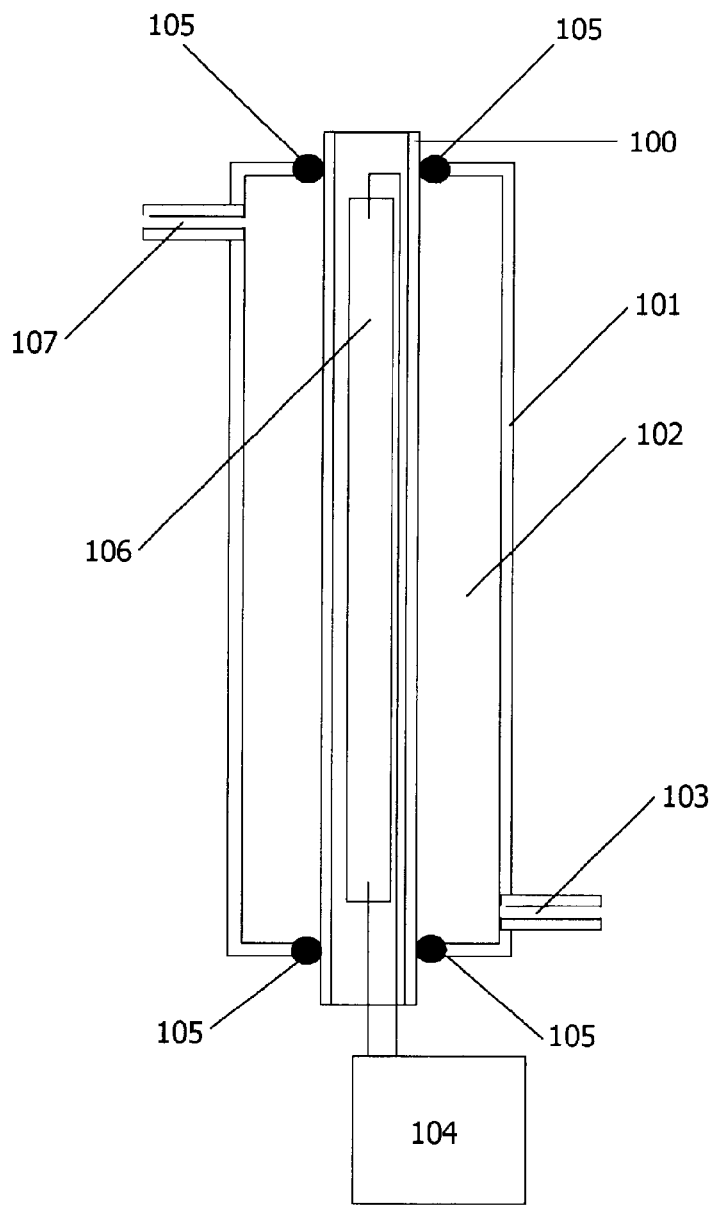
FIG. 1 is a cross-section of a typical photo-chemical reactor for UV radiation of water.

The invention relates to a DBD lamp used in fluid treatment systems, where the irradiated fluid is used as a low voltage outer electrode instead of a metallic wire mesh. It must be noted that any fluid which is electrically conductive may be used. In the following description, numerous specific details are set forth to provide a more thorough description of embodiments of the invention. It is apparent, however, to one skilled in the art, that the invention may be practiced without these specific details. In other instances, well known features have not been described in detail so as not to obscure the invention.

In one or more embodiments of the present invention an electrically conductive fluid, for example water that is not de-ionized, is directly used as a grounded electrode for the DBD lamp. FIG. 3 shows a cross-section of a DBD lamp/reactor according to the present invention. Here fluid 301 which is not already de-ionized is placed inside a metal reactor vessel 300. This fluid 301 is filled in the reactor via fluid inlet 303, and after the procedure leaves the reactor via fluid outlet 306. DBD source 305 is placed inside the reactor vessel, and is sealed using O-ring seals 302 at appropriate places. The entire unit is powered using power supply 304. DBD source 305 has a first dielectric barrier 308 and a second dielectric barrier 307 that enclose a region containing gas 309. An inner electrode 310 is coupled to the first dielectric barrier 308 and fluid 301 serves as an outer electrode coupled to the second dielectric barrier 307.

Figure 2A:
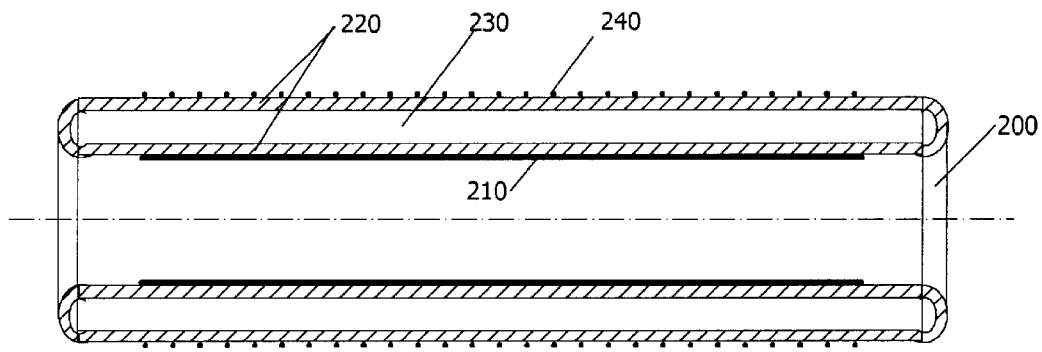
FIG. 2A is a side-on view of a typical coaxial DBD lamp.
Figure 2B:
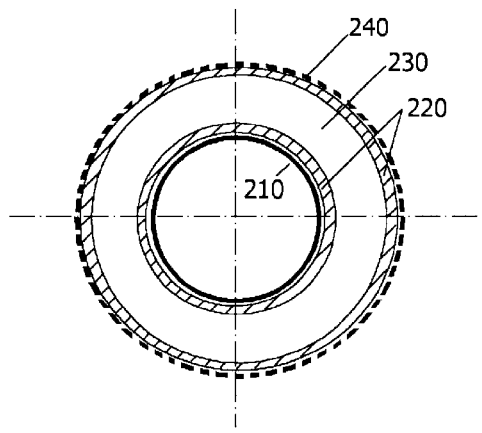
FIG. 2B is an end-on view of a typical coaxial DBD lamp.

Fluid 301 of FIG. 3 is in direct contact with the outer surface of the DBD light source. Since the fluid is a good conductor of electricity, it is used as a low grounded electrode for the DBD lamp. Essentially this fluid replaces the metallic wire mesh outer electrode of prior art DBD lamps such as wire mesh 240 of FIG. 2. By replacing the metallic wire mesh outer electrode with fluid, the invention has a two-fold advantage. First, the fluid provides a strong built-in cooling source for the lamp at no extra cost. This allows to drive the DBD light source at high electrical power (>1 Wcm$^{-2}$) without forced cooling of the light source as in prior art lamps. This greatly increases the efficiency of the excimer production. Second, the absence of the metallic wire mesh increases the amount of emitted radiation, since no radiation is lost due to absorption by the metallic mesh or the quartz sleeve.

In comparison to using a DBD lamp with a mesh electrode (which cover 50% of the lamp surface) in an system as shown in FIG. 1, the radiant power, as well as the efficiency of a DBD source is thereby more than doubled by using fluid as the outer grounded electrode. With a lamp/reactor assembly as shown in FIG. 3, efficiencies of 16–30% (at high power densities) can be generated with sinusoidal high voltages, as compared to 8–15% in prior art lamps that have the metallic mesh.

The inner high voltage electrode remains in the center of the coaxial tube assembly like in the prior art lamps, and provides high voltage across the gas to generate excimer formation. The fluid is sealed against the lamp envelope by two O-ring seals 302, and the fluid is flown through the reactor for processing.

Industrial Applicability

DBD lamps have emerged as novel UV light sources that emit radiation into spectrally selective narrow wavelength bands. The most viable excimers are $Xe_2$, XeCl, XeBr and KrCl whose narrow-banded emission peaks at 172 nm, 308 nm, 282 nm and 222 nm. Typical UV radiant efficiencies of these UV sources amount to 8–15% using a outer mesh electrode and AC high voltage, but with the present invention the radiant efficiency can be greatly increased (16–30%), and at the same time, strong cooling is provided at no extra cost. Both improvements allow this UV source to be used for high-powered application in water treatment, and to extend the amount of possible selective wavelengths (172 nm, 222 nm, 282 nm and 308 nm) for technical UV processing of water in large scales.

As mentioned earlier, water can be replaced by any other fluid which has electrical conductive properties for other kinds of applications. Also, the DBD lamp may be filled with different kinds of gases in order to obtain an intense and spectrally selective radiation in a narrow wavelength range depending on the application. The spectrally selective radiation may range, for example, in the UV, (V)UV, Infrared, visible light, or any other applicable range.

Thus, a DBD lamp used in fluid treatment systems is described in conjunction with one or more specific embodiments. The invention is defined by the following claims and their full scope of equivalents.

What is claimed is:

1. A dielectric barrier discharge-driven light source comprising:
   a first and second dielectric barrier which enclose a gas;
   an inner electrode coupled to an outside portion of said first dielectric barrier; and
   an outer electrode coupled to an outside portion of said second dielectric barrier where said outer electrode is comprised of an electrically conductive fluid.

2. The light source of claim 1 wherein said first and second dielectric barriers have a circular shape.

3. The light source of claim 2 where said circular shape is a coaxial tube.

4. The light source of claim 1 wherein said inner electrode is a high voltage electrode.

5. The light source of claim 1 wherein said outer electrode is water that is not deionized.

6. The light source of claim 4 wherein said high voltage electrode provides high voltage across said gas to generate excimer formation.

7. The light source of claim 1 wherein said electrically conductive fluid acts as a low grounded electrode.

8. The light source of claim 1 wherein said electrically conductive fluid is in direct contact with said outer surface of said dielectric barrier discharge-driven light source.

9. The light source of claim 1 wherein said dielectric conductive fluid provides a strong built-in cooling source that allows said dielectric barrier discharge-driven light source to be driven at electric powers greater than 1 $Wcm^{-2}$ without forced cooling of said light source.

10. The light source of claim 1 wherein said electrically conductive fluid eliminates the absorption of UV radiation from said outer surface of said dielectric barrier discharge-driven light source, thereby more than doubling the efficiency of said dielectric barrier discharge-driven light source.

11. The light source of claim 1 wherein said gas produces an intense, spectrally selective radiation in a narrow wavelength range.

12. The narrow wavelength range of claim 11 is UV, (V)UV, Infrared, or visible light range.

* * * * *